(12) United States Patent
Riley et al.

(10) Patent No.: US 7,390,662 B2
(45) Date of Patent: Jun. 24, 2008

(54) METHOD AND APPARATUS FOR PERFORMING PLATELET MEASUREMENT

(75) Inventors: John S. Riley, Miami, FL (US); Jose Cano, Miami, FL (US); Valentin Quesada, Miami, FL (US); Maritza Lavernia, Miami, FL (US); Mark A. Wells, Davie, FL (US); Eileen Landrum, Miami, FL (US); Carlos A. Perez, Miami, FL (US); Christophe Godefroy, Miramar, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 231 days.

(21) Appl. No.: 11/270,865

(22) Filed: Nov. 9, 2005

(65) Prior Publication Data

US 2007/0105231 A1    May 10, 2007

(51) Int. Cl.
*G01N 31/00* (2006.01)
*G01N 33/48* (2006.01)

(52) U.S. Cl. .................. 436/10; 436/8; 436/17; 436/63; 436/150; 436/164; 435/2; 356/337

(58) Field of Classification Search ............ 436/8, 436/10, 17, 63, 149, 150, 164; 435/2, 4, 435/29; 356/337, 441
See application file for complete search history.

(56) References Cited

U.S. PATENT DOCUMENTS

| | | | |
|---|---|---|---|
| 3,955,890 A | 5/1976 | Bessis et al. | |
| 4,202,625 A | 5/1980 | Weiner et al. | |
| 4,412,004 A | 10/1983 | Ornstein et al. | |
| 4,577,964 A | 3/1986 | Hansen | |
| 5,559,037 A | 9/1996 | Kim et al. | |
| 5,798,827 A | 8/1998 | Frank et al. | |
| 5,817,519 A | 10/1998 | Zelmanovic et al. | |
| 5,891,734 A | 4/1999 | Gill et al. | |
| 6,025,201 A | 2/2000 | Zelmanovic et al. | |
| 6,060,322 A | 5/2000 | Horton et al. | |
| 6,133,995 A | 10/2000 | Kubota | |
| 6,743,634 B2 * | 6/2004 | Kramer | 436/63 |
| 6,784,981 B1 * | 8/2004 | Roche et al. | 356/39 |
| 6,798,508 B2 | 9/2004 | Kramer | |
| 2004/0197232 A1 | 10/2004 | Kramer | |
| 2005/0176152 A1 | 8/2005 | Lopez et al. | |

OTHER PUBLICATIONS

Kim, Y.R., et al., "Isovolumetric Sphering of Erythrocytes for More Accurate and Precise Cell Volume Measurement by . . .", Cytometry, vol. 3, No. 6, pp. 419-427 (1983).

(Continued)

*Primary Examiner*—Maureen M Wallenhorst
(74) *Attorney, Agent, or Firm*—Cuspa Technology Law Associates; Mitchell E. Alter

(57) ABSTRACT

The present invention relates to a hematology instrument system that discriminates platelets from red blood cells, debris and other particles within a blood sample. The instrument system uses an optical trigger and collects data at optical sensor locations relative to a flow cell-illuminating laser beam's optical axis. An axial sensor measures axial light loss due to a particle in the flow cell's illumination aperture. In addition, the instrument system can include an RF unit generates electrical parameters, such as DC and RF parameters, within the flow cell. Blood specimens can be prepared with and without a sphering agent.

22 Claims, 4 Drawing Sheets

OTHER PUBLICATIONS

Kubota, F., "Analysis of red cell and platelet morphology using an imaging-combined flow cytometer", Clin. Lab. Haem., 25, pp. 71-76 (2003).

Machin, S.J., et al., "Platelet Transfusion", Thrombosis and Haemostatis, 74(1), pp. 246-252 (1995).

* cited by examiner

METHOD AND APPARATUS FOR PERFORMING PLATELET MEASUREMENT

FIELD OF THE INVENTION

The present invention relates to a new optical measurement-based hematology system for performing platelet analysis. Axial light loss can be used to quantify the platelets in the analyzed blood sample. In addition, a prescribed light scatter triggering mechanism can be used to enable the sampling of cells smaller than two femtoliters.

BACKGROUND OF THE INVENTION

Most blood analyzer systems in use today count platelets by means of electrically and/or optically based measurements. In an electrical or impedance-based measurement system, particles within a carrier fluid passing through a detection aperture of a flow cytometer cause the generation of electrical pulses proportional to their volume. Using a thresholding technique on the pulses, the particles that gave rise to the pulses are classified as platelets, erythrocytes (red blood cells or RBCs), or leukocytes (white blood cells or WBCs) and debris. Although, in most cases, an electrically based measurement system provides relatively accurate results, it is not without its limitations.

For example, an impedance-based measurement analyzer is not capable of discriminating between platelets and interfering particles, such as microcytes, schistocytes (fragmented RBCs), debris and electronic noise, which leads to falsely high platelet counts. Conversely, platelet aggregates and oversized platelets may fall outside an upper size threshold and be classified as RBCs, which leads to falsely low platelet readings.

In order to determine the course of treatment of a patient, it is generally mandated clinical practice to obtain a very accurate platelet count. For example, if the platelet count is extremely low (e.g., in a range of from 5,000 to 20,000 platelets per microliter), it may become necessary to transfuse platelets or to forego surgery. On the other hand, the critical threshold for a pregnant woman is considerably higher (e.g., favorable platelet counts should be in excess of 140,000 platelets per microliter).

In a typical hematology analyzer, a mathematical fit is performed on the platelet volume distribution between two and twenty fL in order to expand the dynamic range, e.g., up to seventy fL. Except for a platelet count in which part of the distribution is derived, an accurate platelet count cannot be obtained if the raw data does not fit a logarithmic distribution, the mean platelet volume is outside its normal range, the mode is outside its normal range, or if the upper end of the platelet distribution is not decreasing. In such instances, the sample is flagged, and only those platelets lying in the two to twenty femtoliters (fL) range are reported.

Difficulty in obtaining an accurate platelet count at relatively low levels may also be due to poor discrimination of DC noise, smaller RBCs, and coincident passage of RBCs and platelets through the flow cell's detection aperture. Platelet distributions can also shift with respect to volume, depending upon the age of the platelets, thereby changing the shape of the distribution and potentially leading to incorrect extrapolations; since the average lifetime of platelets is only three to five days, the shift can be fairly rapid. As described below, resolution of platelets by other (e.g., optically based) techniques, such as differential light scattering, can help to reduce these discrepancies.

Examples of various types of optically-based prior art schemes for counting platelets include the system described in the U.S. patent to Bessis et al, U.S. Pat. No. 3,955,890, which details a system to collect scattered light and measure its intensity at a minimum of two different azimuthal angles. This patent discloses that while spherical particles produce circular scattering patterns, an elongated RBC passing through a detection aperture scatters light in an ellipsoidal pattern, which is oriented in such a way that its major axis is perpendicular to the major axis of the elongated cell. Consequently, this system allows a determination of light scatter ratios for angles collected perpendicular to one another, as well as determining the length-to-width ratios for individual RBCs and other cellular entities.

U.S. Patent to Weiner et al, U.S. Pat. No. 4,202,625 describes a system for using light scatter to discriminate RBCs by amplifying noise, platelet pulses and RBC pulses, and comparing them to a predetermined noise threshold. The relative amplitudes of the respective signals represent either platelets or RBCs.

U.S. Patent to Ornstein et al, U.S. Pat. No. 4,412,004 discloses a method for isovolumetrically sphering and fixing RBCs, thereby eliminating the effect of shape on the determination of their respective and collective volumes, as determined by using different angles of forward light scatter. This technique is also addressed in the publication Cytometry 3/6, 1983, pp 419-427, which describes that, by using high and low angle light scatter, both normal and abnormal RBC samples produce greater separation between sphered RBCs and platelets, as compared to RBCs that are unsphered.

U.S. Patent to Hansen, U.S. Pat. No. 4,577,964 describes a system wherein low angle scatter is used to discriminate platelets from RBCs, based on cell volume, cell refractivity, and duration of the scattered light.

In another patent relating to the determination of leukocytes and nucleated red blood cells (NRBC), U.S. Pat. No. 5,559,037 (to Kim et al.) discloses a method for flow cytometric analysis of nucleated red blood cells and leukocytes. The method comprises lysis of red blood cells and NRBC cytoplasm from a whole blood sample to expose the nucleated red blood cell nuclei to a vital nuclear stain and minimizing the permeation of the vital nuclear stain into the leukocytes and analyzing the sample by measuring fluorescence and two angles of light scatter. This method features a triple triggering method which blocks signals from debris (fluorescent and non-fluorescent) and identifies the signals which fall below the axial light loss (ALL) trigger but above the fluorescence trigger (FL3) as NRBCs. This method requires heating of the reagent to 42° C. in order to obtain the NRBC and leukocyte differentiations.

U.S. Patent to Frank et al, U.S. Pat. No. 5,798,827, describes a system for determining the shape of individual RBCs by measuring the asymmetry of the light scatter pattern produced by laser illumination of the cell collected in specific angular quadrants.

U.S. Patents to Zelmanovic et al, U.S. Pat. Nos. 5,817,519 and 6,025,201 describe light scattering-based platelet discrimination systems, in which light scattering is measured over a high angle interval of five to twenty degrees and a low angle interval of one to five degrees. First and second optical channel light scattering signals are converted to platelet volume values and a refractive index of the platelets, which is converted into a platelet component concentration value. A platelet dry mass value is calculated as a product of the platelet component concentration value and the platelet volume. Histograms are then formed of the platelet volumes, the platelet component concentrations and the platelet dry masses. Platelets are resolved from non-platelets, and platelet parameters are determined by the presence of light scatter-based platelet signals within a volume versus refractive index map.

U.S. Patent to Gill et al, U.S. Pat. No. 5,891,734 describes an automated hematology and fluorescent cytometry system that detects and counts RBCs and platelets using an impedance flow transducer, and also uses multi-angle light scatter and fluorescence to count and differentiate platelets or platelet aggregates or both within an optical flow transducer.

U.S. Patent to Horton et al, U.S. Pat. No. 6,060,322 details an optical system for identifying reticulated RBCs and platelets through the use of a reagent composition that contains a nucleic acid dye and a sphering agent.

U.S. Patent to Kubota, U.S. Pat. No. 6,133,995 describes a light scattering-based blood analyzer, which generates a distribution diagram on the basis of a plurality of parameters extracted from each particle in a sample. A cluster including platelets is separated from other information in the distribution diagram, and a discriminator calculates a discrimination function for the separated cluster including the platelets, and for discriminating the platelets from other particles in the cluster on the basis of the distance from the calculated discrimination function, to produce a count of the number of platelets.

From the above-listed patents and from commercially available equipment for conducting optical platelet measurements, it will be appreciated that optically-based platelet measurement systems employ several approaches for performing optical platelet counts. Typically, optical-based schemes employ at least one low angle forward scatter measurement to determine the volume of the particle.

It should be noted that when light interacts with a particle, some of the incident light changes direction through the scattering process (i.e. light scatter) and part of the light is absorbed by the particles. Both of these processes remove energy from the incident beam. When viewed along the incident axis of the beam, the light loss is called extinction or axial light loss.

The above-referenced patent to Weiner et al teaches that red cells and platelets can be separated using light scatter, and it should be noted that light scatter and light loss are physically different measurements. This is no different than the distinction regarding fluorescence signals, which is another resultant signal produced when light interacts with a particle. For further edification attention may be directed to the publication by H. C. van de Hulst, "Light Scattering by Small Particles", copyright 1957, Dover Publications Inc., NY.

As a non-limiting example, the Ortho ELT-8 system uses a single light scatter measurement. The CELL-DYN® 4000 manufactured by Abbott Laboratories, the assignee of the above-referenced Gill et al Patent, couples a second scatter measurement, orthogonal light scatter (SS), to determine the internal complexity of the particle in an effort to eliminate non-platelet particles from the platelet count. The Advia 120 system, manufactured by Bayer Corp., the assignee of the above-referenced Patents to Zelmanovic et al, adds a second forward light scatter measurement, which determines the particle's index of refraction for platelet identification. The XE-2100 system manufactured by Sysmex Corp., the assignee of the above-referenced Kubota Patent, identifies platelets through an additional fluorescent measurement of cells stained with a fluorescent dye. It should be noted that it is generally recognized that immunological identification of platelets allows counting of true platelets in the presence of large numbers of confounding particles. The above-referenced CELL-DYN 4000 also allows for an immunological measurement using monoclonal antibody CD-61.

SUMMARY OF THE INVENTION

The present invention relates to a method of discriminating and quantifying platelets from non-platelet particles in a blood sample comprising the steps of a) passing a blood sample through an aperture of a blood sample transport path; (b) directing a light beam through said aperture; (c) analyzing said blood sample in said aperture by measuring axial light loss signals; and(d) reporting platelets in said blood sample on the basis of said signal obtained in step (c).

In a preferred embodiment, the blood sample is analyzed by both axial light loss and a light scatter parameter such as lower median angle light scatter signals.

In both embodiments described above, an optical trigger is used such as an axial light loss trigger or a lower median angle light scatter trigger.

In another embodiment, the invention is directed to a method of discriminating and quantifying platelets from non-platelet particles in a blood sample comprising the steps of (a) passing a blood sample through an aperture of a blood sample transport path; (b) directing a light beam through said aperture; (c) detecting axial light loss from said blood sample passing through said aperture; (d) measuring at least one parameter of said light beam in response to an axial light loss trigger signal obtained from detecting said axial light loss in step (c); and (e) reporting platelets in said blood sample on the basis of said measured parameter obtained in step (d).

In a further preferred embodiment, the present invention of discriminating and quantifying platelets from non-platelet particles in a blood sample includes triggering on the detection of axial light loss and measuring axial light loss and at least one other parameter selected from the group of parameters consisting of side scatter of said light beam, mini median angle light scatter, and lower median angle light scatter of said light beam through the flow cell of the apparatus.

Pursuant to a preferred embodiment of the present invention, prior to being introduced into the instrument system, a whole blood specimen is diluted in an isotonic RBC sphering agent, and then gradually mixed prior to aspiration into the system.

Figure 1:
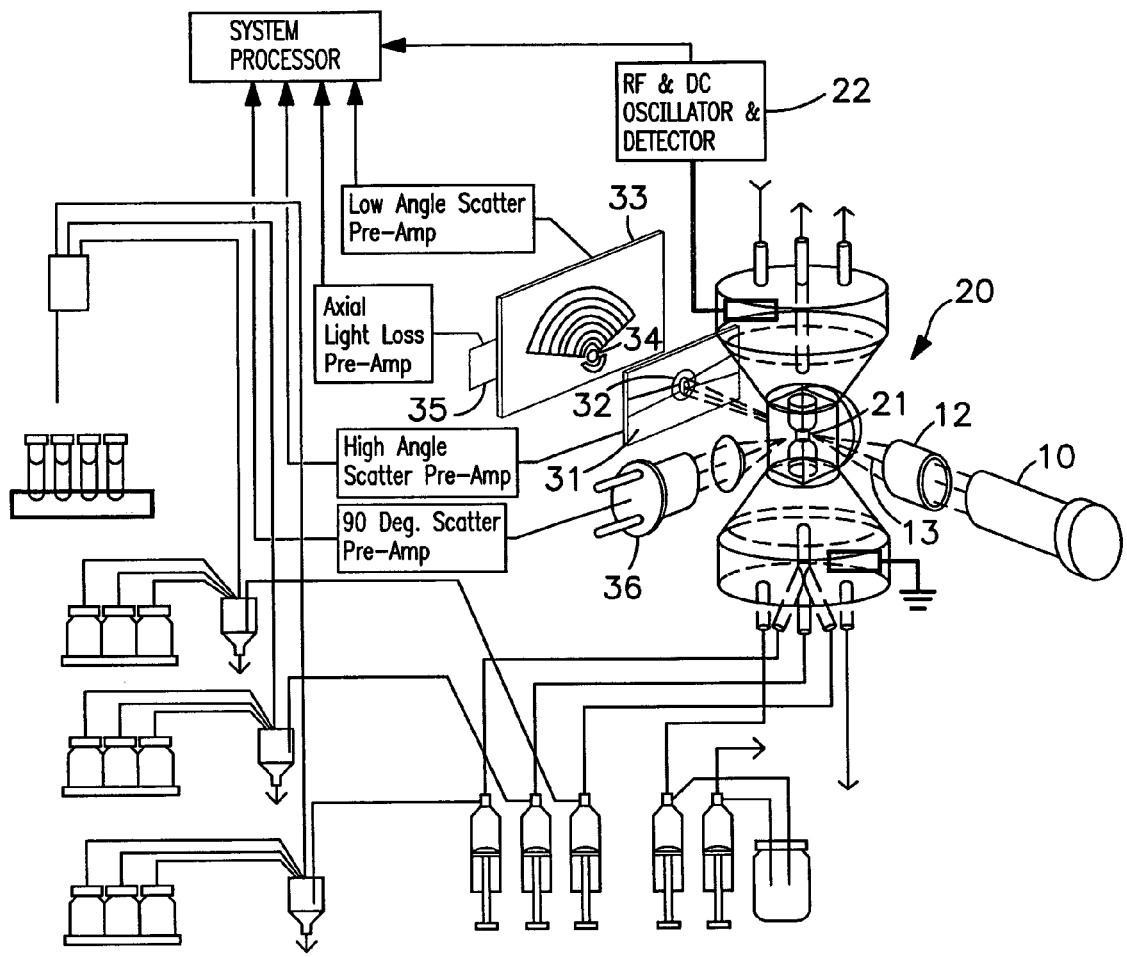
FIG. 1 is a diagrammatic perspective view of the overall architecture of a VCS flow cytometer or automated hematology system in accordance with a preferred embodiment the present invention.
Figure 6:
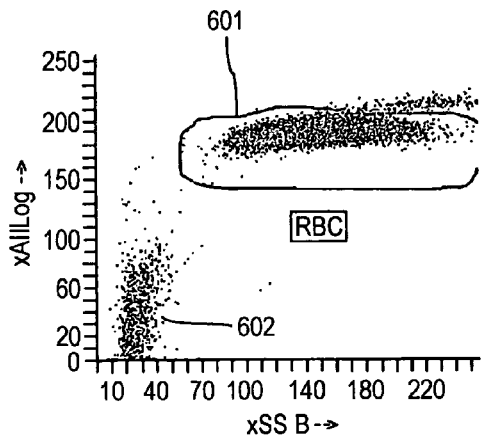
FIG. 6 is a plot of axial light loss vs. side scatter obtained from a prepared whole blood sample containing a sphering reagent and measured using the automated hematology system of FIG. 1, in which red blood cell and platelet populations are readily distinguished.
Figure 8:
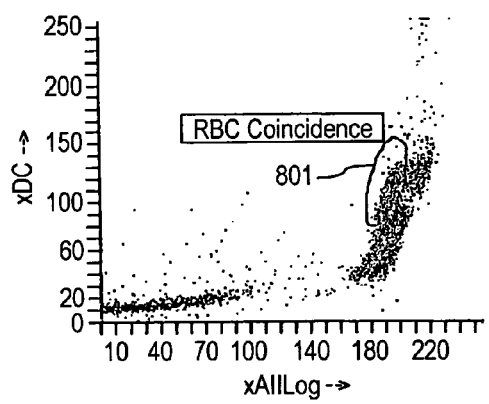
Figure 9:
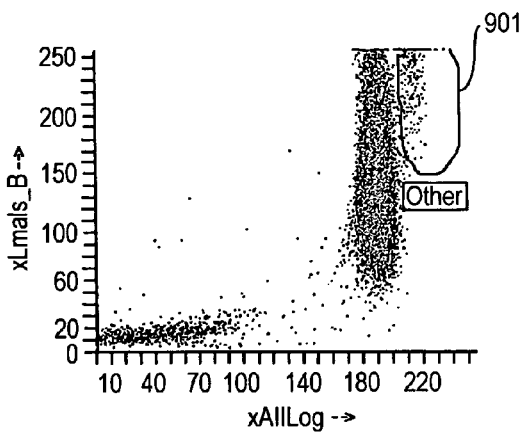
Figure 10:
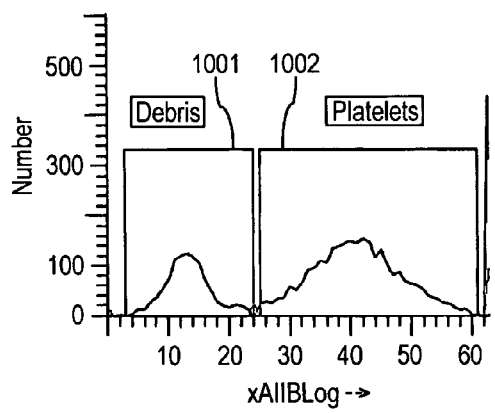
Figure 11:
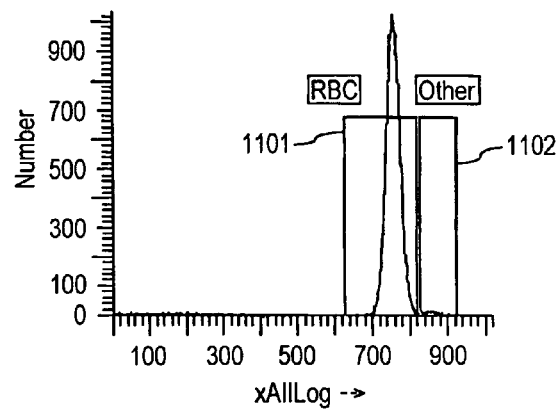
Figure 12:
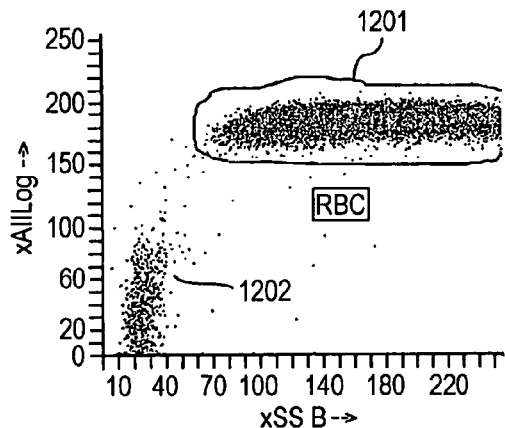
Figure 13:
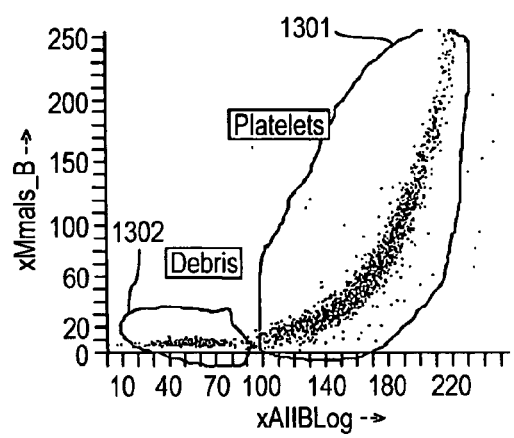
Figure 14:
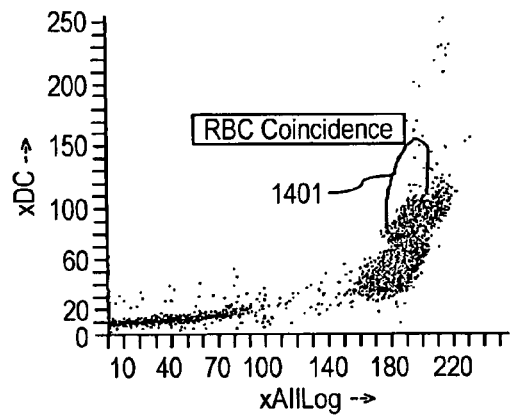
Figure 15:
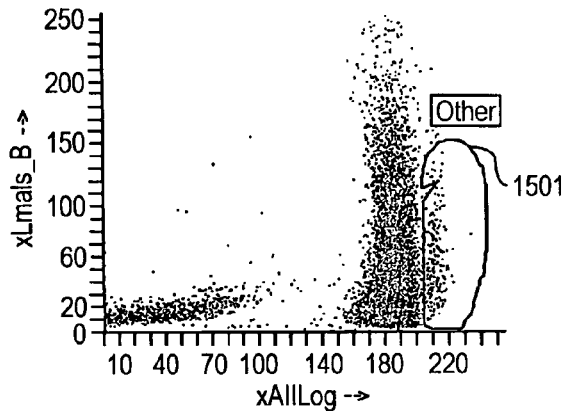
Figure 16:
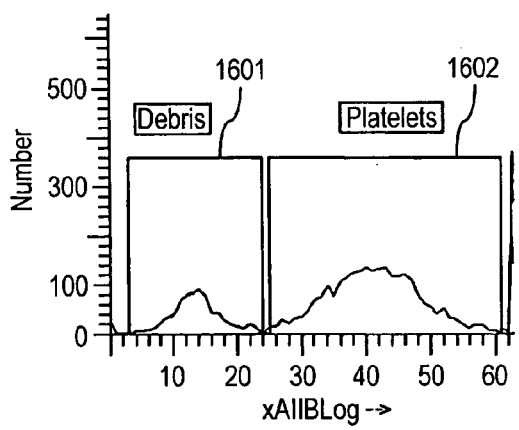
Figure 17:
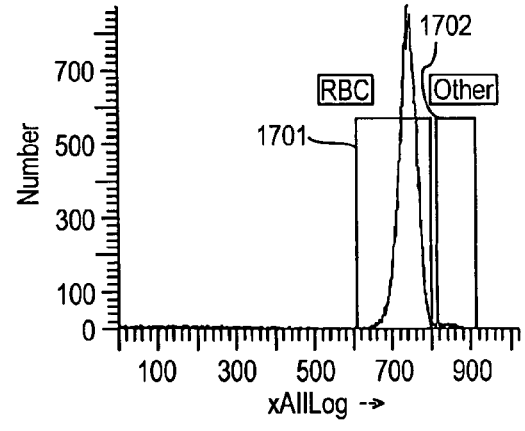

6, measured using the automated hematology system of FIG. 1, in which platelet and debris populations are readily distinguished;

FIG. 8 is a plot of DC voltage vs. axial light loss of the prepared whole blood sample shown in FIG. 6, measured using the automated hematology system of FIG. 1, showing the presence of overlapping or coincident RBCs;

FIG. 9 is a plot of lower median angle light scatter vs. axial light loss of the prepared whole blood sample shown in FIG. 6, measured using the automated hematology system of FIG. 1, in which other particle populations are readily distinguished from RBCs;

FIG. 10 is a histogram showing distributions of adjacent debris and platelet populations in axial light loss of the prepared whole blood sample shown in FIG. 6, measured using the automated hematology system of FIG. 1;

FIG. 11 is a histogram showing distributions of adjacent RBC and other particle populations in axial light loss of the prepared whole blood sample shown in FIG. 6, measured using the automated hematology system of FIG. 1;

FIG. 12 is a plot of axial light loss vs. side scatter obtained from a prescribed whole blood sample not containing a sphering reagent and measured using the automated hematology system of FIG. 1, in which red blood cell and platelet populations are readily distinguished;

FIG. 13 is a plot of lower median angle light scatter vs. axial light loss of the prescribed whole blood sample shown in FIG. 12, measured using the automated hematology system of FIG. 1, in which platelet and debris populations are readily distinguished;

FIG. 14 is a plot of DC voltage vs. axial light loss of the prescribed whole blood sample shown in FIG. 12, measured using the automated hematology system of FIG. 1, showing the presence of overlapping or coincident RBCs;

FIG. 15 is a plot of lower median angle light scatter vs. axial light loss of the prescribed whole blood sample shown in FIG. 12, measured using the automated hematology system of FIG. 1, in which other particle populations are readily distinguished from RBCs;

FIG. 16 is a histogram showing distributions of adjacent debris and platelet populations in axial light loss of the whole blood sample shown in FIG. 12, measured using the automated hematology system of FIG. 1; and FIG. 17 is a histogram showing distributions of adjacent RBC and other particle populations in axial light loss of the whole blood sample shown in FIG. 12, measured using the automated hematology system of FIG. 1.

DETAILED DESCRIPTION

In the present description, it is to be understood that low angle light scatter signal is less than 10°, and preferably in a range from about 1° to about 7° off the beam axis of the incident light. Lower median angle light scatter is approximately from 6° to 26° and preferably from 9° to 20° and upper median angle light scatter is approximately from 15° to 50° preferably 21° to 43° off the beam axis of the incident light.

Axial light loss (ALL, also known as forward extinction) is generally the decrease in light energy due to a particle passing through a beam of incident light and being detected by a photo-detector. When the beam of incident light strikes a particle, the light is either scattered or absorbed, both of which remove energy from the incident light and the incident beam is attenuated. This attenuation is referred to as extinction. When viewed along the axis of the beam of incident light, it is referred to as axial light loss. Generally ALL signals are detected at an angle from about 0° to about 1° from the incident light. In a preferred embodiment of the present invention, ALL signals are collected in a circular area less than about 0.5° from the incident light axis. ALL signals are strongly influenced by the size of a cell or particle.

Since axial light loss measurement measures the loss of energy from the beam of incident light, whereas low angle light scatter measurement measures the increase in light, different electronic circuitries are required for measuring these two different optical properties. The electronic circuitry used for measuring the ALL signals uses an inverting amplifier, whereas the electronic circuitry used for measuring the low angle light scatter signals uses a non-inverting amplifier.

An optical detector assembly is used for measuring the ALL and light scatter signals. Many designs of the optical detection hardware can be used for the purpose of the present invention. In one embodiment, the optical detector assembly includes two discrete photo-detectors, of appropriate size and geometry, placed on a printed circuit board (PCB). One photo-detector is used for measuring the ALL signals, and the other photo-detector is used for measuring the light scatter signals. Signals from the photo-detectors are sent to conditioning circuitry within an experimental hematology analyzer which is described hereinafter.

In another embodiment, the optical detector assembly includes a planar photodiode array with sensing regions of appropriate size and geometry for measuring the ALL and light scatter signals. Signals from the photodiode array are sent to conditioning circuitry within the experimental hematology analyzer. In a further embodiment, the optical detector assembly includes a fiber optic array for measuring the ALL and light scatter signals. As a non-limiting example, the fiber optic array described in detail in U.S. Pat. No. 6,798,508, the disclosure of which is incorporated herein, may be employed.

The hematology system of the invention contains a laser illumination source the light output beam of which is directed at an aperture of a flow cell, through which a carrier fluid containing a blood sample to be analyzed passes. Spatially distributed around the flow cell is a plurality of optical sensors for scattered light collection. Along the laser beam axis, a first, generally planar optical sensor which is an optical detector, serves as a median angle light scatter detector, which collects individual angular ranges of scattered light of lower median angle light scatter on the order of from approximately 6° to 26°, preferably 9° to 20° off the beam axis, and upper median angle light scatter on the order of from approximately 15° to 50°, preferably 21° to 43° off the beam axis, yielding a composite optimum working range on the order of from approximately 9° to 43° off the beam axis. The geometric center of the first optical sensor is coincident with the beam axis of the illuminating laser. This optical detector has an opening about its geometric center to allow the passage of the light that has passed through the aperture and scattered light not sensed on the first optical sensor.

A second optical sensor in the form of a multi-element photodiode array is located directly behind the first optical sensor, with the center of the second optical sensor being coincident with the laser beam axis, so that the second optical sensor is coaxially aligned with the first optical sensor. The second optical sensor collects light signals from angular regions of from 0 to 1.1°, 1.2° to 3.3°, 3.3° to 4.6° and 4.6° to 6.1° off the beam axis, yielding a composite range from 0° to 6.1° off the beam axis.

The center element of the second optical detector provides a light extinction parameter known as axial light loss. This parameter is implemented as a single signal in this embodiment, but can be implemented using multiple signals.

The multiple axial light loss signals are useful in providing trigger and measurement parameters for embodiments containing more than one illumination source and each having a unique emission wavelength. The measured axial light loss parameter results from the presence of a particle in the flow cell's illumination aperture upon which the laser beam is directed.

A third optical sensor, in the form of a photomultiplier tube assembly and fitted with an optical element, is positioned to capture light scattered orthogonal to or at 90° relative to the beam axis or side scatter.

The outputs of the sensors described above are coupled through associated amplifier channels, to produce twelve parameters, that are digitized and coupled to a system control and analysis processor. These parameters include six unique optical measurements. The preferred optical measurements include lower median angle light scatter of approximately 9°-20°, upper median angle light scatter of approximately 21° to 43° with a composite of the lower median angle light scatter and upper median angle light scatter resulting in a median angle light scatter of approximately (9°-43°), mini median angle light scatter on the order of 1.2°-6.1° and orthogonal (or about 90°) light scatter also referred to as side scatter (SS), and axial light loss (about 0°-1.1°).

Four of the light scattering parameters are collected at two gain settings. One is at a prescribed low gain for RBCs and the other is at a prescribed high gain for platelets. This can be used to supplement or eliminate the use of mathematical transformations, such as logarithms to fit both RBCs and platelet events onto one view for any particular angle of light scatter. As a consequence the gain setting and signal processing electronics may be readily customized for a platelet and for a red blood cell setting.

As opposed to the common practice of having a VCS hematology analyzer to capture data based upon an electrical (impedance) trigger, the system of the present invention employs a novel triggering method. The new triggering method includes using an optical light trigger, such as axial light loss trigger and lower median angle light scatter trigger. The choice of triggering on the optical light is based upon the fact that DC and RF channels are capable of resolving only those cells that are larger than platelets from the noise of the instrument. As a consequence, triggering on those electrical parameters for cells the size of platelets or smaller will result in irregular signals, which are often indistinguishable from system noise.

On the other hand, optical sensors have low system noise and are capable of resolving platelet-sized cells. With the optical sensors, platelet signals are easily identified from noise providing a triggering source that does not have the problems of the prior art. The sensitivity of the optical triggering method used in this embodiment will further benefit by the use of solid state lasers which generate a lower level of optical noise.

Before detailing the optical platelet measurement system of the present invention, it should be observed that the present invention resides primarily in a prescribed arrangement of conventional automated hematology system components in a novel combination, together with control and analysis software. Consequently, the configurations of these components and the manner in which they are interfaced with software of the automated hematology system are shown in the drawings by a readily understandable pictorial system diagram.

In addition, the collected parameter relationship figures associated with predefined test samples show only those specific aspects that are pertinent to describing the present invention, so as not to obscure the disclosure with details which would be readily apparent to those skilled in the art having the benefit of the description herein. Thus, the pictorial diagram of FIG. 1 is primarily intended to show the major components of the automated hematology system of the present invention in a convenient functional grouping, so that the architecture, functionality and operation of the present invention can be more readily understood.

As described above, a blood test sample is diluted to form a sample mixture and analyzed in a flow cell by measuring axial light loss. The platelets are differentiated from other cell types by using the obtained axial light loss signals.

The sample mixture can also be analyzed in a flow cell by measuring lower median angle light scatter and axial light loss signals. The platelets will be differentiated from other cell types by using the obtained lower median angle light scatter and axial light loss signals.

FIG. 1 shows the overall architecture of an experimental VCS™ flow cytometer or automated hematology system in accordance with a preferred embodiment of the present invention. As shown in FIG. 1, an optical detector assembly is used for measuring the ALL and light scatter signals.

As shown in FIG. 1, the system comprises an illumination source 10, which is operative to produce an output optical beam that is directed at an illumination aperture or window 21 of a flow cell 20, through which a carrier fluid containing a blood sample to be analyzed passes. As a non-limiting example, illumination aperture 21 may comprise a square internal (50 micron) and square external (0.167") geometry window, while the illumination source 10 may comprise a Uniphase Model No. 1122P, 2 mW HeNe laser. The laser output beam is focused by a focusing lens 12 along a beam axis 13 onto the flow cell aperture 21. An unit 22 including a solid state RF is used to generate both DC and RF electrical parameters within the flow cell.

Spatially distributed around the flow cell are a plurality of optical sensors for light collection. In particular, a first, generally planar optical sensor 31 serves as a median angle light scatter (LS2) detector, and is operative to collect individual angular ranges of light scattered off the beam axis on the order of from 9° to 20°, and on the order of from 21° to 43°, thus yielding a composite range on the order of from 9° to 43°. The geometric center 32 of the first optical sensor 31 is coincident with the beam axis 13 of the illuminating laser 10.

A second light optical sensor 33 comprises a multi-element photodiode array that is located directly behind the first optical sensor 31. The second optical sensor 33, has a center 34 which is coincident with the laser beam axis 13, so that the second optical sensor 33 is coaxially aligned with the first optical sensor 31. The second optical sensor 33 collects scattered light from angular regions of from 1.2° to 3.3°, 3.3° to 4.6° and 4.6° to 6.1°, yielding a composite range from 1.2° to 6.1° off the beam axis.

A third optical sensor 35 has a detection window coincident with the laser beam axis 13. The third optical sensor is positioned directly behind the second optical sensor and measures axial light loss resulting from the presence of a particle in the flow cell's illumination aperture 21 upon which the laser beam is directed.

A fourth optical sensor 36, such as a photomultiplier tube assembly, is positioned to capture light scattered orthogonal to or at 90° relative to the beam axis 13.

The outputs of the sensors described above are coupled through associated amplifier channels to produce a total of twelve parameters listed below in Table 1. The parameters are digitized and coupled to a system processor.

TABLE 1

| NO. | NAME | DESCRIPTION |
|---|---|---|
| 1 | DC | Particle Volume |
| 2 | RF | Conductivity |
| 3 | LS1 | Light Scatter Angle (21°-43°) |
| 4 | LS2 | Light Scatter Angle (9°-43°) |
| 5 | ALL (RBC Gains) | Axial Light Loss (0°-1.1°) |
| 6 | ALL (Platelet Gains) | Axial Light Loss (0°-1.1°) |
| 7 | LS3 (RBC Gains) | Light Scatter Angle (9°-20°) |
| 8 | LS3 (Platelet Gains) | Light Scatter Angle (9°-20°) |
| 9 | LS4 (RBC Gains) | Light Scatter Angle (1.2°-6.1°) |
| 10 | LS4 (Platelet Gains) | Light Scatter Angle (1.2°-6.1°) |
| 11 | Orthogonal/Side Scatter SS (RBC Gains) | 90° Light Scatter |
| 12 | Orthogonal/Side Scatter SS (Platelet Gains) | 90° Light Scatter |

Table 1 lists six unique light angles (LS1, LS2, ALL, LS3, LS4 and Orthogonal SS) with four of the angles provided at two gains—one for RBCs and one for platelets. These parameters were measured using the LS3 light scattering channel trigger.

Figure 2:
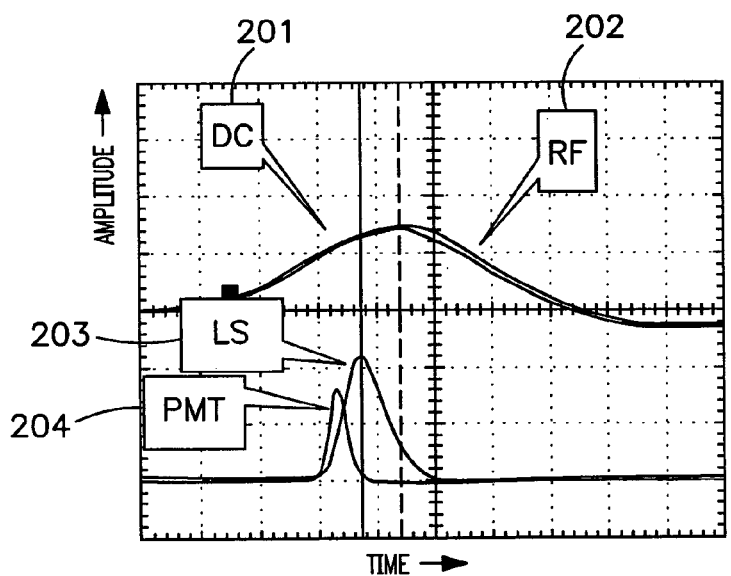
FIG. 2 shows the variation with time of pulse waveforms associated with light scatter channels and electrical channels.

In addition to employing optical sensors, the apparatus includes an unit having a solid state RF to generate electrical parameters, including both DC and RF parameters within the flow cell. A comparison of using optical light channels vs. electrical channels for triggering is shown in FIG. 2. In particular, pulse traces 201 and 202 show impedance waveforms produced by the passage of a particle through the flow cell aperture representative of a change in DC impedance and a change in RF impedance, respectively. Pulse traces 203 and 204 show optical waveforms produced by a particle through the flow cell aperture representative of a change in optical light including ALL and lower median angle light scatter (indicated as LS in the figure), and a change in side scatter light detected by a photo multiplier tube (indicated as PMT in the figure), respectively.

In FIG. 2, the relative time displacements between the impedance waveforms 201 and 202 and the optical waveforms 203 and 204 are a function of their relative alignments, sensor characteristics and their respective sensing zone length.

As further shown in FIG. 2, the sensors are mutually aligned. Typically, the sensors are considered to be mutually aligned, if the phase difference between waveform peaks are within a prescribed time window (e.g., less than about five microseconds).

The data acquisition system employed in this invention is programmed such that if all waveform peaks are located within a predetermined time window, then one of them can be designated as a master reference pulse to trigger the acquisition sequence to initiate data collection from both the master and the remaining 'slave' parameter waveforms.

The signal-to-noise ratio will vary for each type of sensor employed. For example, the DC and RF waveforms 201 and 202 are capable of resolving only those cells that are larger than platelets from the instrument noise. As a consequence, triggering on these parameters for cells the size of platelets or smaller will result in signals which are often indistinguishable from system noise.

On the other hand, optical sensor waveforms 203 and 204 resolve platelet-sized cells. The optical sensor produces low system noise so that platelet signals are easily distinguished from instrument noise. Therefore, the optical sensor provides a reliable triggering source.

Studies by the inventors have demonstrated that the LS3 parameter listed in Table 1 provides the sensitivity and low noise required for platelet data collection. It has been further found that the ALL parameter can be used to identify the platelet population. It should be noted that although the DC and RF parameters are not used for triggering, they are still useful in identifying cell populations and they enhance the platelet analysis.

In accordance with a preferred embodiment of the present invention, whole blood specimens are diluted in an isotonic RBC sphering agent prior to being analyzed by the flow cytometer system.

Figure 3:
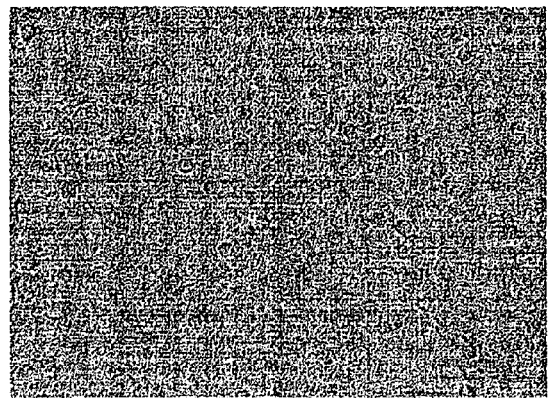
FIG. 3 shows an image of a preparation of whole blood in an isotonic sphering reagent diluted at a ratio of 1:1.
Figure 4:
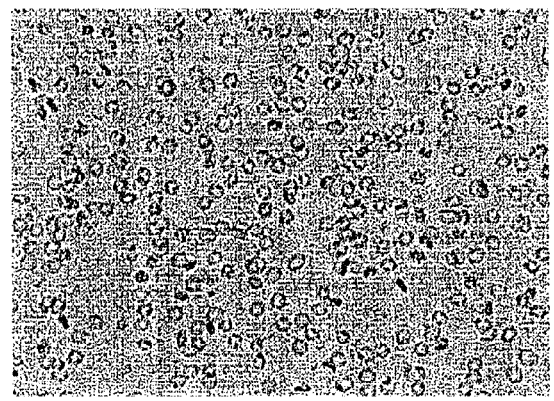
FIG. 4 shows an image of a preparation of whole blood in Beckman Coulter, Inc. ISOTON® III Diluent, diluted at a ratio of 1:1.
Figure 5:
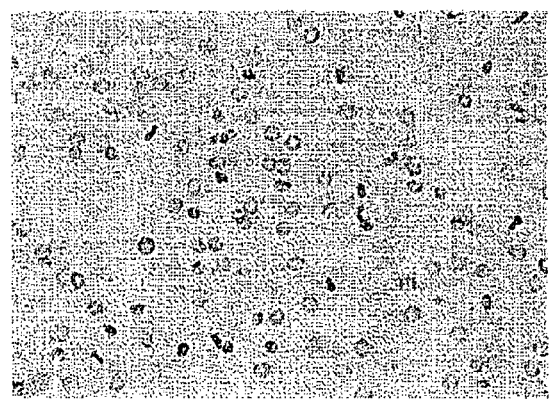
FIG. 5 shows a preparation of whole blood, diluted at a ratio of 1:1 with Beckman Coulter, Inc. ISOTON IIIE Diluent that is formaldehyde free.

To evaluate the effect of different reagents on the RBC and platelet populations, aliquots of the same whole blood sample were mixed with different isotonic solutions and observed under a microscope. FIGS. 3, 4 and 5 depict the resulting microscopic images captured at 40 times magnification.

In particular, FIG. 3 shows an image of a preparation of whole blood in an isotonic sphering reagent system containing a formaldehyde component diluted at a ratio of 1 part blood to one part isotonic sphering reagent system. In this preparation, the RBCs are uniformly sphered.

FIG. 4 shows an image of a preparation of whole blood in Beckman Coulter, Inc. ISOTON III Diluent, containing a formaldehyde component but not containing a sphering agent diluted at a ratio of 1:1. This image reveals that RBCs are not as uniform as those shown in FIG. 3 and have ellipsoidal shapes.

FIG. 5 shows a preparation of whole blood, diluted at a ratio of 1:1 with Beckman Coulter, Inc. ISOTON IIIE Diluent that is formaldehyde-free. This image also reveals that RBCs are not as uniform as those shown in FIG. 3.

Therefore, as shown by these Figures, the use of an isotonic sphering agent system is optional for the optical differentiation of platelets. However, a sphering agent provides better results than if it was not included.

FIGS. 6-17 represent a variety of collected data population relationships for both sphered and non-sphered samples. FIGS. 6-11 are sphered blood cell samples and 12-17 are non-sphered blood cell sample. These figures show the manner in which the data is analyzed to differentiate the platelet population.

Sample data was collected at a sixteen-bit analog-to-digital resolution and a total of 50,000 events were collected for each run. Two gating strategies are shown, with trade-offs between minimizing the number of required parameters and optimizing overall performance.

The preferred gating strategies employs a plurality of (five) parameters, specifically, LS3, LS4, side scatter (SS), DC, and axial light loss (ALL). However, pursuant to the present invention, an optical platelet measurement can be obtained using only the ALL parameter with an ALL or a lower medium angle light scatter trigger.

Axial light loss (ALL) and side scatter (SS) parameters are processed in two separate channels having different gain settings (one of which is optimized for platelets, and the other of which is optimized for RBCs). As described above, the use of a sphering agent serves to make the RBC population more uniform, which assists in the gating strategy. The use of an electrical parameter, such as DC parameter allows additional measurements, such as platelet volume, to be reported. In addition, the DC parameter helps identify overlapping or coincident RBCs.

FIGS. 6-9 show a preferred gating strategy, while FIGS. 10 and 11 show a less preferred gating strategy. In FIGS. 6-11, the whole blood sample has been mixed with a sphering reagent.

In accordance with the preferred approach, FIG. 6 depicts side scatter (SS) vs. axial light loss (ALL) to differentiate the RBC and platelet populations. In particular, in FIG. 6, the RBC population is shown by the surrounding gate 601, while the remnant 602 in the vicinity of the origin corresponds to the platelet population.

Figure 7:
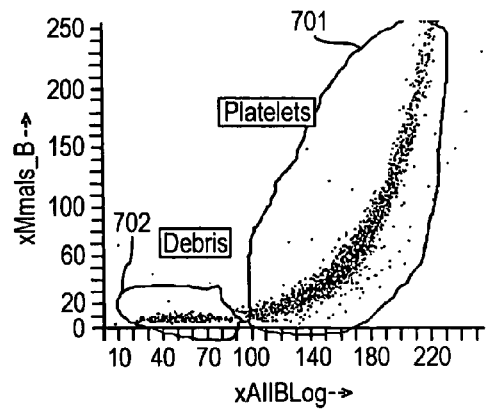
FIG. 7 is a plot of lower median angle light scatter vs. axial light loss of the prepared whole blood sample shown in FIG.

FIG. 7 shows the manner in which the platelet population is distinguished from debris by using ALL and LS4 (mini medium angle light scatter, indicated as Mmals in the figure). Specifically, in FIG. 7, the platelet population is shown by the surrounding gate 701, while the debris population is shown by the surrounding gate 702.

FIG. 8 shows the presence of overlapping or coincident RBCs the plot of axial light loss and DC. In particular, overlapping RBCs are shown by the gating region 801.

FIG. 9 shows the relationship between ALL and LS3 (lower medium angle light scatter, indicated as Lmals in the figure) with a gating region 901 surrounding particles other than RBCs and platelets.

An examination of FIGS. 6-9 reveals that axial light loss (ALL) is a parameter that is common to each gating strategy. In accordance with the present invention, advantage is taken of this axial light loss commonality to allow the use of this parameter independently of all other parameters to provide the required analysis for platelet counting.

This finding is illustrated in FIGS. 10 and 11, which are histograms showing distributions of adjacent debris and platelet populations (respectively at 1001 and 1002 in FIG. 10), and distributions of adjacent RBC and other particle populations (respectively at 1101 and 1102 in FIG. 11).

FIGS. 12-15 show a preferred gating strategy, while FIGS. 16 and 17 show a less preferred gating strategy. In FIGS. 12-17, the whole blood sample has not been mixed with a sphering reagent.

Again, pursuant to a preferred approach, depicted in FIG. 12, side scatter (SS) vs. axial light loss (ALL) is used to differentiate the RBC and platelet populations. In FIG. 12, the RBC population is depicted by the surrounding gate 1201, while the remnant 1202 in the vicinity of the origin corresponds to the platelet population.

FIG. 13 shows the manner in which the platelet population without a sphering reagent may be distinguished from debris, using ALL and LS4 (mini medium angle light scatter, indicated as Mmals in the figure). Specifically, in FIG. 13, the platelet population is noted by the surrounding gate 1301, while the debris population is noted by the surrounding gate 1302.

FIG. 14 shows the presence of overlapping or coincident RBCs the plot of axial light loss and DC. In particular, overlapping RBCs are noted by the gating region 1401.

FIG. 15 shows the relationship between ALL and LS3 (lower medium angle light scatter, as indicated as Lmals in the figure) with a gating region 1501 surrounding particles other than RBCs and platelets.

As in the case of FIGS. 6-9, an examination of FIGS. 12-15 reveals that axial light loss (ALL) is a parameter that is common to each gating strategy. Again, in the case of a non-sphering reagent diluted blood sample, advantage is taken of this axial light loss commonality to allow the use of this parameter independently of all other parameters to provide the required analysis for platelet counting. Therefore, the only parameter required to gate all of the populations of FIGS. 12-15 is axial light loss. This is diagrammatically illustrated in FIGS. 16 and 17, which are respective histograms showing distributions of adjacent debris and platelet populations (respectively at 1601 and 1602 in FIG. 16), and distributions of adjacent RBC and other particle populations (respectively at 1701 and 1702 in FIG. 17).

While we have shown and described an embodiment in accordance with the present invention, it is to be understood that the same is not limited thereto but is susceptible to numerous changes and modifications as known to a person skilled in the art. We therefore do not wish to be limited to the details shown and described herein, but intend to cover all such changes and modifications as are obvious to one of ordinary skill in the art.

What is claimed:

1. A method of differentiation of platelets from non-platelet particles in a blood sample comprising:
    (a) diluting a blood sample with a reagent to form a sample mixture;
    (b) passing said sample mixture through an aperture of a flow cell;
    (c) directing a light beam at said aperture;
    (d) measuring axial light loss signals from said platelets and said non-platelet particles in said sample mixture passing through said aperture; and
    (e) differentiating said platelets from said non-platelet particles in said blood sample using optical signals consisting of said axial light loss signals obtained in(d).

2. The method of claim 1, wherein said measuring axial light loss signals is performed at two different gain settings.

3. The method of claim 2, wherein said gain settings include a low gain setting for red blood cells and a high gain setting for platelets.

4. The method of claim 1 further comprising obtaining an absolute count of said platelets using a known volume of said blood sample.

5. The method of claim 1, wherein said reagent is a diluent or a sphering reagent.

6. A method of differentiation of platelets from non-platelet particles in a blood sample comprising:
    (a) diluting a blood sample with a reagent to form a sample mixture;
    (b) passing said sample mixture through an aperture of a flow cell;
    (c) directing a light beam at said aperture;
    (d) measuring axial light loss signals and light scatter signals in the angular range from 9° to 20° from said platelets and said non-platelet particles in said sample mixture passing through said aperture; and
    (e) differentiating said platelets from said non-platelet particles in said blood sample using a combination of said axial light loss signals and said light scatter signals in an angular range from 9° to 20° obtained in (d).

7. The method of claim 6 further comprising in (d) measuring light scatter signals in an angular range from 1.2° to 6.1° from said platelets and said non-platelet particles in said sample mixture passing through said aperture; and in (e) differentiating said platelets from said non-platelet particles in said blood sample using a combination of obtained said axial light loss signals and said light scatter signals in the angular range from 9° to 20° and from 1.2° to 6.1°.

8. The method of claim 6 further comprising in (d) measuring light scatter signals about 90° from said light beam from said platelets and said non-platelet particles in said sample mixture passing through said aperture; and in (e)

differentiating said platelets from said non-platelet particles in said blood sample using a combination of obtained said axial light loss signals and said light scatter signals in the angular range from 9° to 20° and about 90° from said light beam.

9. The method of claim 6, wherein said measuring axial light loss signals and said light scatter signals is performed at two different gain settings.

10. The method of claim 9, wherein said gain settings include a low gain setting for red blood cells and a high gain setting for platelets.

11. The method of claim 6, wherein said measuring axial light loss signals and said light scatter signals is triggered by an axial light loss triggering signal.

12. The method of claim 6, wherein said measuring axial light loss signals and said light scatter signals is triggered by a light scatter triggering signal in the angular range from 9° to 20°.

13. The method of claim 6 further comprising obtaining an absolute count of said platelets using a known volume of said blood sample.

14. The method of claim 6, wherein said reagent is a diluent or a sphering reagent.

15. A method of differentiation of platelets from non-platelet particles in a blood sample comprising:

(a) diluting a blood sample with a reagent to form a sample mixture;

(b) passing said sample mixture through an aperture of a flow cell;

(c) directing a light beam at said aperture;

(d) measuring axial light loss signals, electrical impedance signals, and light scatter signals of said platelets and said non-platelet particles in said sample mixture passing through said aperture; and (e) differentiating said platelets from said non-platelet particles in said blood sample using a combination of said axial light loss signals, said impedance signals and one or more said light scatter signals selected from the group consisting of forward light scatter and side scatter signals obtained in (d).

16. The method of claim 15, wherein said forward light scatter signals are in an angular range from 9° to 20°, or from 1.2° to 6.1° from said light beam, respectively.

17. The method of claim 15, wherein said measuring axial light loss signals and said light scatter signals is performed at two different gain settings.

18. The method of claim 17, wherein said gain settings include a low gain setting for red blood cells and a high gain setting for platelets.

19. The method of claim 15, wherein said measuring axial light loss signals and said light scatter signals is triggered by an axial light loss triggering signal.

20. The method of claim 15, wherein said measuring axial light loss signals and said light scatter signals is triggered by a light scatter triggering signal in an angular range from 9° to 20°.

21. The method of claim 15 further comprising obtaining an absolute count of said platelets using a known volume of said blood sample.

22. The method of claim 15, wherein said reagent is a diluent or a sphering reagent.

* * * * *